(12) United States Patent
Metscher

(10) Patent No.: US 7,735,310 B2
(45) Date of Patent: Jun. 15, 2010

(54) GAS TURBINE AND METHOD FOR SHUTTING OFF A GAS TURBINE WHEN BREAKAGE OF A SHAFT IS IDENTIFIED

(75) Inventor: Martin Metscher, Munich (DE)

(73) Assignee: MTU Aero Engines GmbH, Munich (DE)

( * ) Notice: Subject to any disclaimer, the term of this patent is extended or adjusted under 35 U.S.C. 154(b) by 32 days.

(21) Appl. No.: 11/664,356

(22) PCT Filed: Sep. 17, 2005

(86) PCT No.: PCT/DE2005/001640

§ 371 (c)(1),
(2), (4) Date: Mar. 30, 2007

(87) PCT Pub. No.: WO2006/037286

PCT Pub. Date: Apr. 13, 2006

(65) Prior Publication Data

US 2008/0178573 A1    Jul. 31, 2008

(30) Foreign Application Priority Data

Oct. 1, 2004 (DE) .......... 10 2004 047 892

(51) Int. Cl.
*F02G 3/00* (2006.01)
(52) U.S. Cl. .......... 60/39.091; 415/14
(58) Field of Classification Search .......... 60/39.091, 60/776, 779, 790, 39.281, 39.282, 734; 415/14, 415/16, 18
See application file for complete search history.

(56) References Cited

U.S. PATENT DOCUMENTS

| | | | |
|---|---|---|---|
| 2,815,818 A | | 12/1957 | Douglass |
| 2,977,758 A | * | 4/1961 | Haworth et al. .......... 60/796 |
| 3,023,575 A | * | 3/1962 | McCombs, Jr et al. .......... 60/790 |
| 3,159,166 A | * | 12/1964 | Luedemann et al. .......... 137/71 |
| 3,696,612 A | * | 10/1972 | Berman .......... 60/786 |
| 4,406,117 A | * | 9/1983 | Rowen et al. .......... 60/39.27 |
| 4,718,229 A | * | 1/1988 | Riley .......... 60/39.281 |
| 4,870,270 A | * | 9/1989 | Brennan .......... 250/227.21 |
| 5,301,499 A | * | 4/1994 | Kure-Jensen et al. .......... 60/773 |

(Continued)

FOREIGN PATENT DOCUMENTS

DE    2 062 047    7/1972

(Continued)

*Primary Examiner*—Michael Cuff
*Assistant Examiner*—Phutthiwat Wongwian
(74) *Attorney, Agent, or Firm*—W. F. Fasse; W. G. Fasse

(57) ABSTRACT

A gas turbine, such as an aircraft engine, has at least one compressor, at least one turbine, a combustion chamber, and a fuel pump to supply fuel to the combustion chamber. Upon identification of a break of a shaft that couples a compressor with a turbine, the gas turbine is shut off. For this purpose, at least one electrical current conductor is arranged on the shaft, whereby this current conductor is a component of a current supply for the fuel pump or for a fuel pump regulation. When the integrity of the current conductor is disrupted, thereby the current supply of the fuel pump or of the fuel pump regulation is interrupted in order to automatically shut off the gas turbine.

16 Claims, 2 Drawing Sheets

U.S. PATENT DOCUMENTS

| | | | |
|---|---|---|---|
| 5,411,364 A | 5/1995 | Aberg et al. | |
| 5,953,901 A * | 9/1999 | Sidiropoulos | 60/39.091 |
| 6,494,046 B1 * | 12/2002 | Hayess | 60/779 |
| 7,002,172 B2 | 2/2006 | Rensch | |
| 7,043,896 B2 * | 5/2006 | Matthews | 60/39.091 |
| 7,100,354 B2 * | 9/2006 | Opper | 60/39.091 |
| 2003/0091430 A1 | 5/2003 | Mulera et al. | |

FOREIGN PATENT DOCUMENTS

| | | |
|---|---|---|
| DE | 195 24 992 | 8/1996 |
| DE | 197 27 296 | 1/1999 |
| DE | 103 10 900 | 9/2004 |
| GB | 1 239 349 | 7/1971 |
| GB | 1 374 988 | 11/1974 |
| GB | 2 303 225 | 2/1997 |
| JP | 03-121219 | 5/1991 |
| SU | 1 229 563 | 5/1986 |

* cited by examiner

GAS TURBINE AND METHOD FOR SHUTTING OFF A GAS TURBINE WHEN BREAKAGE OF A SHAFT IS IDENTIFIED

FIELD OF THE INVENTION

The invention relates to a gas turbine and to a method for shutting off a gas turbine upon identification of a shaft break.

BACKGROUND INFORMATION

Gas turbines, such as aircraft engines for example, comprise at least one compressor and at least one turbine in addition to a combustion chamber. In gas turbines that comprise only a single compressor as well as a single turbine, the compressor and the turbine are connected with one another by a single rotating shaft. If the gas turbine has two compressors as well as two turbines, namely a low pressure compressor, a high pressure compressor, a high pressure turbine as well as a low pressure turbine, then the low pressure compressor as well as the low pressure turbine are connected with one another by a first shaft, and the high pressure compressor as well as the high pressure turbine are connected with one another by a second shaft. The two shafts then generally extend coaxially relative to one another, whereby one of the two shafts surrounds the other.

Overspeeding rotation conditions of a gas turbine as a result of a shaft break must be surely avoided. If a shaft break arises, then a compressor coupled with the broken shaft will no longer take-up any power from the corresponding turbine, whereby an overspeeding rotation of the turbine is caused. Because considerable damages can be caused on the gas turbine by the overspeeding rotation conditions, shaft breaks must be surely detected or identified, in order to shut off the gas turbine as a reaction thereto.

The DE 195 24 992 C1 discloses a method for regulating a shaft engine with a micro-control device with monitoring of the engine for shaft break and overspeeding rotation. According to the method disclosed therein, rotational speeds are measured with the aid of sensors, and the engine is tested with respect to shaft breakage and overspeeding rotation on the basis of these rotational speeds. If such an erroneous function is recognized, then the fuel delivery to the combustion chamber is interrupted and the gas turbine is deactivated.

In connection with the method disclosed in DE 195 24 992 C1, the determination of a difference rotational speed between a compressor-side end or section and a turbine-side end or section of the gas turbine shaft is necessary. Accordingly, rotational speeds must be detected at least two points, at a first compressor-side point and at a second turbine-side point. Especially in the hot turbine area, a rotational speed determination requires complicated provisions, whereby carrying out the method known from the prior art has been shown to be expensive and complicated. Furthermore, the method known from DE 195 24 992 C1 is only applicable on one or two-shafted gas turbines. On the other hand, this method known from the prior art is not practicable for multi-shafted gas turbines. This especially applies to more than two-shafted gas turbines, because a shaft surrounded by rotating shafts cannot easily without further efforts be referenced to a stationary reference system.

SUMMARY OF THE INVENTION

Beginning from this, the problem underlying the present invention is to provide a novel gas turbine and a novel method for shutting off a gas turbine upon identification of a shaft break thereof.

This problem is solved by a gas turbine according to the present invention, wherein at least one electrical current conductor is arranged on a shaft, whereby the electrical current conductor is a component of an electrical current supply for the fuel pump or a component of an electrical current supply for a fuel pump regulation, whereby the integrity of the or each current conductor is monitored in such a manner that upon a change of the integrity of the or each current conductor, the current supply of the fuel pump or the current supply of the fuel pump regulation is interrupted, in order to shut off the gas turbine in a self-acting or automatic manner.

A shaft break can be surely and easily detected in the inventive gas turbine. In comparison to the prior art, in the inventive gas turbine no separate arrangement is necessary in order to shut off the gas turbine upon a shaft break. Rather, in the invention, the gas turbine can be shut off directly from the integrity monitoring of the or each current conductor. This increases the reliability and reduces the costs.

The above problem has further been solved by the inventive method for shutting off a gas turbine upon identification of a shaft break thereof, wherein the method proceeds as set forth herein.

DETAILED DESCRIPTION OF AN EXAMPLE EMBODIMENT OF THE INVENTION

Figure 1:
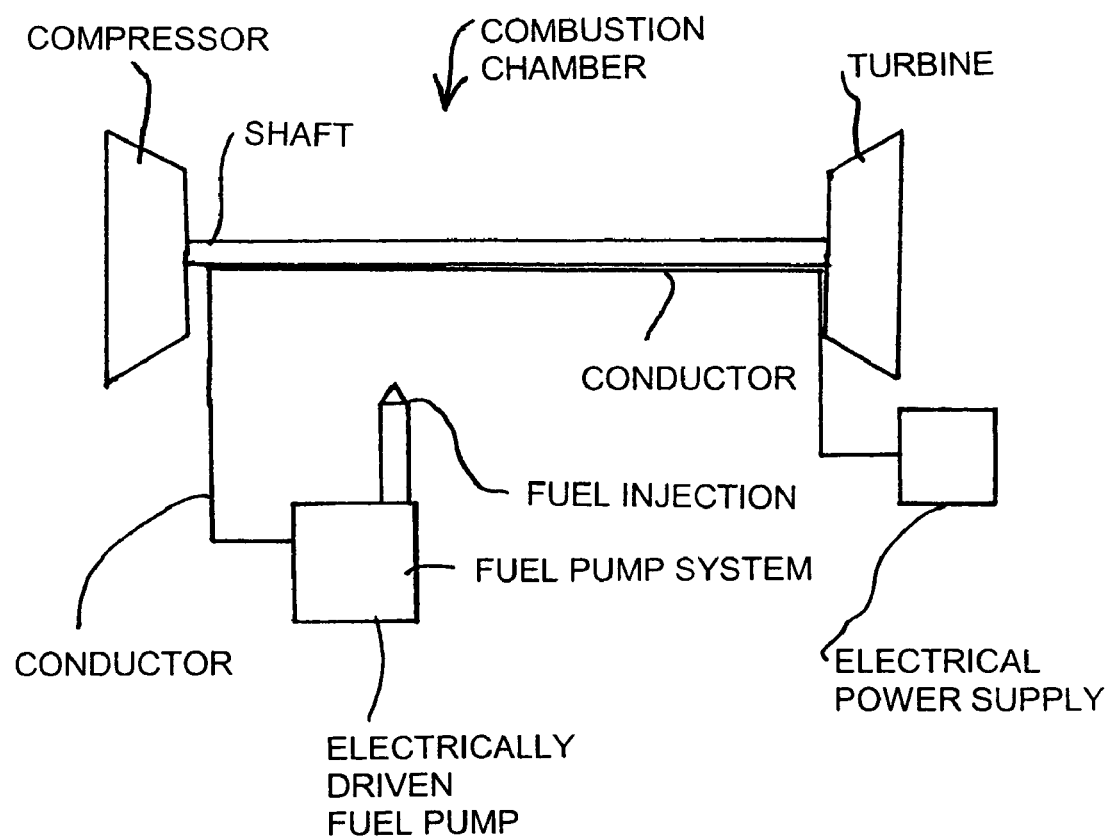
FIG. 1 is a schematic diagram representing the arrangement of the major components of a gas turbine according to an embodiment of the invention.

In the simplest example embodiment of the present invention, a gas turbine is proposed, which has a compressor, a turbine and a combustion chamber, whereby the compressor and the turbine are connected with one another via a shaft, and whereby fuel is introduced into the combustion chamber via a fuel pump as schematically shown in FIG. 1. Now, in order to shut off the gas turbine to avoid overspeeding rotation conditions upon the occurrence of a shaft break of the shaft that couples the compressor and the turbine with one another, in the sense of the present invention it is proposed to arrange at least one electrical current conductor on the shaft. For an electrically driven fuel pump, the electrical current conductor is directly a component of an electrical current supply for the fuel pump. For a mechanically driven fuel pump, to which an electrical fuel pump regulation is allocated, the electrical current conductor is a component of an electrical current supply for the fuel pump regulation as schematically shown in FIG. 2.

If now a shaft break arises, then the integrity of the or each current conductor will also be changed, whereby upon a change of the integrity of the or each current conductor, the current supply of the fuel pump or the fuel pump regulation will be automatically interrupted, in order to shut off the gas turbine. If the current conductor is a component of the current supply of the fuel pump, then upon a shaft break and therewith a break of the current conductor, the current supply of the fuel pump will be directly interrupted. If the current conductor is a component of the current supply of the fuel pump regulation, then upon a shaft break and therewith a break of the current conductor, the fuel pump regulation is directly interrupted. In both cases, thereby the gas turbine can be shut off directly, that is to say without a further device or arrangement.

It is thus in the sense of the present invention to arrange, on at least one shaft that is to be monitored, at least one electrical current conductor that is a component of an electrical or current circuit. If the or each electrical current conductor is damaged upon occurrence of a shaft break, then the corresponding electrical or current circuit as interrupted and the fuel supply to the combustion chamber can be directly shut-off. From that there arises a simple as well as sure shutting-off of the gas turbine upon a shaft break.

Figure 2:
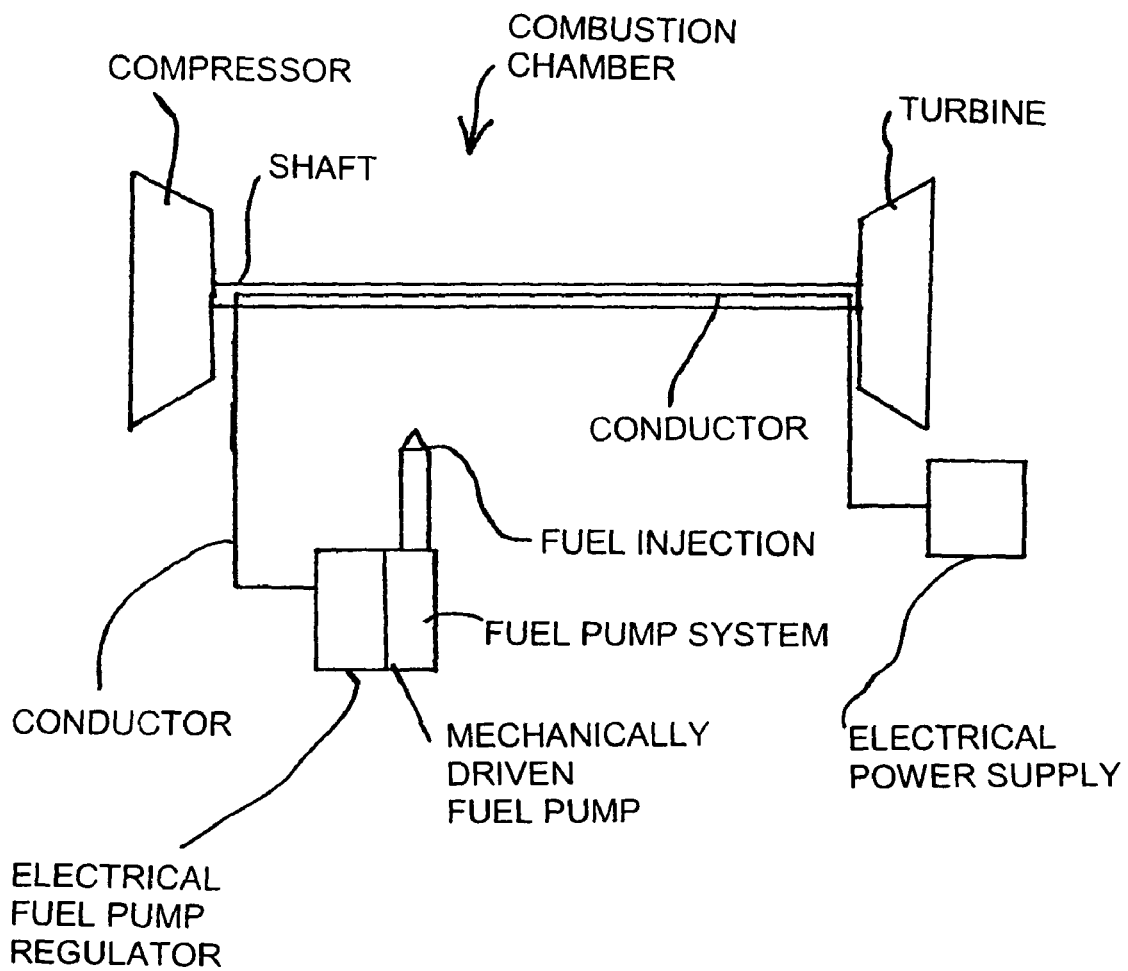
FIG. 2 is a schematic diagram representing other features of the invention in another embodiment.

As schematically shown in FIG. 2, it is further mentioned that the or each current conductor allocated to the rotating shaft can be arranged partially within as well as partially outside of the shaft. Thus, the current conductors can be guided along either an inner side or an outer side of the shaft.

The inventive principle is also applicable to multi-shaft gas turbines in a simple manner. For this purpose, at least one current conductor is allocated to each shaft.

With the aid of the present invention, a sure determination of a shaft break is possible. As a result of that, structural assemblies of the gas turbine, for example the rotors, can be embodied narrower and lighter, which leads to weight savings on the one hand and cost savings on the other hand. Only relatively few components are necessary for determining the shaft break. The inventive system is compactly constructed and detects a shaft break immediately and directly, without having to take further mechanisms into consideration. The invention can be embodied in a redundant manner with simple means. Simply the number of the current conductors being utilized needs to be multiplied. A shaft break is detectable in a simple and sure manner on multi-shaft gas turbines, and as a result the fuel supply to the combustion chamber can be directly shut off.

The invention claimed is:

1. A gas turbine arrangement comprising:
   a compressor;
   a turbine;
   a shaft that couples said turbine with said compressor;
   a combustion chamber interposed between said compressor and said turbine;
   a fuel supply system arranged and adapted to supply a fuel to said combustion chamber; and
   an electrical power supply that includes an electrical conductor and that is adapted to supply electrical power via said electrical conductor to said fuel supply system so as to operate said fuel supply system;
   wherein said electrical conductor is arranged in or on said shaft so that upon occurrence of a shaft break of said shaft said electrical conductor will be disrupted and thereby directly interrupt the supply of electrical power to said fuel supply system and thereby automatically shut-off said gas turbine arrangement.

2. The gas turbine arrangement according to claim 1, wherein said fuel supply system comprises an electrically powered fuel pump, and said electrical conductor is connected to said fuel pump so as to supply electrical power via said electrical conductor to said fuel pump so as to operate said fuel pump.

3. The gas turbine arrangement according to claim 1, wherein said fuel supply system comprises a fuel pump and an electrically powered regulator for said fuel pump, and said electrical conductor is connected to said regulator so as to supply electrical power via said electrical conductor to said regulator so as to operate said regulator.

4. The gas turbine arrangement according to claim 1, wherein said electrical conductor is arranged extending longitudinally along said shaft.

5. The gas turbine arrangement according to claim 4, wherein said electrical conductor is arranged at least partially outside on said shaft.

6. The gas turbine arrangement according to claim 4, wherein said electrical conductor is arranged at least partially within said shaft.

7. The gas turbine arrangement according to claim 1, wherein said electrical conductor is arranged at least partially outside on said shaft.

8. The gas turbine arrangement according to claim 1, wherein said electrical conductor is arranged at least partially within said shaft.

9. The gas turbine arrangement according to claim 3, wherein said fuel pump is mechanically driven.

10. The gas turbine arrangement according to claim 1, including no arrangement other than said electrical conductor for triggering a shut-down of said gas turbine arrangement upon the occurrence of the shaft break.

11. A method of operating and shutting off a gas turbine including a rotational shaft, a fuel supply system arranged and adapted to supply a fuel to a combustion chamber and an electrical power supply that includes an electrical conductor and that is arranged and adapted to supply electrical power via said electrical conductor to said fuel supply system so as to operate said fuel supply system, wherein said electrical conductor is arranged in or on said shaft, and wherein said method comprises the steps: when said shaft and said electrical conductor are intact, supplying electrical power via said electrical conductor to said fuel supply system and thereby operating said fuel supply system; breaking said shaft and thereby also breaking said electrical conductor arranged in or on said shaft due to said breaking of said shaft; interrupting said supplying system of said electrical power via said electrical conductor to said fuel supply due to said breaking of said electrical conductor, and thereby shutting off said gas turbine by shutting off said fuel supply system due to said interrupting of said supplying of said electrical power.

12. The method according to claim 11, wherein said fuel supply system comprises an electrically powered fuel pump, and said electrical conductor is connected to said fuel pump, and comprising supplying electrical power via said electrical conductor to said fuel pump so as to operate said fuel pump.

13. The method according to claim 11, wherein said fuel supply system comprises a fuel pump and an electrically powered regulator for said fuel pump, and said electrical conductor is connected to said regulator, and supplying electrical power via said electrical conductor to said regulator so as to operate said regulator.

14. The method according to claim 11, wherein said electrical conductor is arranged extending longitudinally along said shaft.

15. The method according to claim 14, wherein said electrical conductor is arranged at least partially outside on said shaft.

16. The method according to claim 14, wherein said electrical conductor is arranged at least partially within said shaft.

* * * * *

UNITED STATES PATENT AND TRADEMARK OFFICE
CERTIFICATE OF CORRECTION

| | | Page 1 of 1 |
|---|---|---|
| PATENT NO. | : 7,735,310 B2 | |
| APPLICATION NO. | : 11/664356 | |
| DATED | : June 15, 2010 | |
| INVENTOR(S) | : Metscher | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 27 days.

Column 1,
Line 48, after "detected at", insert --at--;

Column 3,
Line 6, after "circuit", replace "as" by --is--;

Column 4,
Line 38, after "supplying", delete "system";
Line 39, after "supply", insert --system--.

Signed and Sealed this
Twenty-ninth Day of May, 2012

David J. Kappos
*Director of the United States Patent and Trademark Office*